United States Patent [19]

Christensen

[11] Plant 4,762

[45] Sep. 1, 1981

[54] MINIATURE ROSE PLANT

[75] Inventor: Jack E. Christensen, Ontario, Calif.

[73] Assignee: Armstrong Nurseries, Inc., Ontario, Calif.

[21] Appl. No.: 158,354

[22] Filed: Jun. 11, 1980

[51] Int. Cl.[3] ..... A01H 5/00
[52] U.S. Cl. ..... Plt./7
[58] Field of Search ..... Plt./7

*Primary Examiner*—James R. Feyrer

*Attorney, Agent, or Firm*—William H. Elliott, Jr.; Andrew R. Klein

[57] ABSTRACT

A hardy rose plant of the hybrid miniature class, having a vigorous growth habit, and having slightly better than average resistance to mildew, said plant producing, throughout the growing season, a profusion of well-formed buds and flowers, these latter being from about 1 inch to $1\frac{1}{4}$ inches in size and having from 22 to 28 petals plus 2 to 6 petaloids. The overall color effect of the flowers is rather uniformly coral and pink. The flowers are sterile, and do not generally set hips.

1 Drawing Figure

1

This invention relates to a hybrid miniature rose plant of the hardy dwarf type. The plant is a bush outdoor seedling cultivated primarily for garden decoration.

The seed parent was "Gingersnap" (U.S. Plant Pat. No. 4,330) and the pollen parent "Magic Carrousel" (U.S. Plant Pat. No. 3,601). The plant was first propagated in Ontario, Calif., and the descriptive and comparative references to this plant and its bloom hereinafter will relate to plants of the same class grown in this region. This variety preserves its distinguishing characteristics through succeeding propagations, by cuttings and budding.

This new variety is most readily distinguished from its seed parent, Gingersnap, by the combination of the following characteristics. Whereas Gingersnap produces buds and flowers of a brighter orange coloration, the new rose bears buds and flowers of a coral pink coloration essentially as described and illustrated herein. Gingersnap is classified as a hybrid floribunda, whereas the new cultivar falls into the hybrid miniature class. The new rose has an absence of small prickles on all stages of growth, whereas Gingersnap bears small prickles on all growth stages. Whereas Gingersnap bears open flowers of $3\frac{1}{4}$ to 4 inches in diameter, the new cultivar bears significantly smaller open flowers of 1 to $1\frac{3}{4}$ inches in diameter.

The new variety differs from its pollen parent, Magic Carrousel, most notably in the following respects. Magic Carrousel produces buds and flowers of a white and red coloration, whereas the new cultivar has buds and flowers of a relatively uniform coral pink coloration, essentially as described and illustrated herein. Whereas the new rose bears flowers of 22 to 28 petals, Magic Carrousel bears flowers of significantly higher petalage (30 to 40). Whereas the new rose bears only large prickles on all stages of growth, Magic Carrousel bears only a few large prickles on the main stems and a few small prickles on the branches and new shoots.

The flowers are sometimes borne singly, but usually three to five or more to a stem in irregular rounded to pyramidal clusters on strong stems which are medium to long for miniature roses. The plant blooms abundantly outdoors, and nearly continuously during the growing season. The blooms have a slight tea fragrance.

2

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the R.H.S. Color Chart, put out by The Royal Horticultural Society in London.

BUD

The peduncle is short to average length, heavy caliper, erect, stiff and moderately smooth, with some stipitate glands. The color is between Yellow Green, 146A, and Green, 137C, with a reddish blush near Red-Purple, 60A.

Before the calyx breaks, the bud is medium to large in size, for miniature roses, medium-length, pointed and ovoid, with foliaceous appendages and some stipitate glands on the surface of the bud. Usually, slender foliaceous parts extend beyond the tip of the bud one-half or more of its length.

As the calyx breaks, the color is between Red, 43B, and Red, 43C. The inner surface of the sepals carries a fine tomentum; margins are lined with stipitate glands and hairs.

As the first petal opens, the bud is average in size, medium-length, pointed and ovoid. The color on the outside of the petal is between Red, 50B, and Red, 42D, with a basal attachment zone of near Green-Yellow, 1D. The inside surface of the petal is between Red, 43B, and Red, 42D, with a basal attachment zone of the same coloration as on the outside of the petal. The bud opens up well, and is not prevented from opening by cold, hot, wet or dry weather.

BLOOM

The size of the bloom when fully open is average to large, for miniature roses, being from 1 inch to $1\frac{3}{4}$ inches in diameter. Petalage is double, with from 22 to 28 petals, plus 2 to 6 petaloids arranged regularly. The bloom is cupped to high centered at first, becoming open to cupped. At first the petals remain somewhat tightly cupped, with tips reflexed outward, becoming later at maturity somewhat loosely cupped, with tips reflexed outward.

The petals are medium to thick in texture, moderately leathery, with inside slightly satiny and outside slightly shiny. The outside petals are round, with apex flat. Intermediate petals are round to broadly obovate, while inside petals are broadly obovate to irregular. The colors may be modified by being shaded and/or washed with other colors.

The paragraph immediately following describes color values observed in a flower newly opened in the month of October. The plant had been grown outdoors, in Ontario, Calif.

The outer surfaces of all petals, outside, intermediate and inside, were all essentially the same in coloration, being between Red, 50A, and Red, 46D, with a large basal attachment zone of near Green-Yellow, 1D. The inner surfaces of all petals were essentially the same, being between Red, 43B, and Red, 44D, with a smaller basal attachment zone with coloration like that of the outer surface.

The following paragraph describes color values observed in a flower which had been open for three days in the month of October. The plant had been grown outdoors, in Ontario, Calif.

The outer surface of both the outside petal and the inside petal was between Red, 46D, and Red, 50A, with a large basal attachment zone of Green-White, 157D. The inner surface of both the outside petal and the inside petal was between Red, 44D, and Red, 43C, with a smaller attachment zone with the same coloration as the outer surface.

The general color effect of the newly opened flower is between Red, 43B, and Red, 44D. The color effect was between Red, 43C, and Red, 44D, in a flower that had been three days open. The petals persist, fading to near Red, 48D, then the peduncle separates from the stem and the aged flower falls off cleanly. It is not particularly affected by cold, hot, wet or dry weather.

The flower on the bush in the garden persists for from 3 to 5 days in the month of October. Cut roses grown outdoors and kept at living-room temperatures persist for from 4 to 7 days in the month of October.

REPRODUCTIVE ORGANS

The stamens are average in number and are arranged regularly.

The filaments are medium-length, and near Green-Yellow, 1D, in color, washed lightly with Red, 51C. Most are with anthers.

The anthers are medium to large in size, all opening at about the same time. The color just prior to dehiscence is near Yellow-Orange, 15C.

There is a moderate amount of pollen which is near Yellow-Orange, 15C, in color.

The pistils are approximately 35 in number, this being average.

The styles are moderately even, short to average length, average caliper, and loosely bunched.

The stigma is near Red, 45A, in color.

The ovaries are usually all enclosed in the calyx.

This new variety does not naturally set hips in Ontario, Calif., and for that reason no sepals or seeds are described.

FOLIAGE

The compound leaves usually comprise 3 to 5 leaflets. They are from normal to abundant, of medium size for miniature roses, heavy to somewhat leathery and semi-glossy. The leaflets are oval, with apex acute, base round and margin doubly serrate.

The upper surface of the mature foliage is between Green, 131A, and Yellow-Green, 147A, in color. The under surface is near Green, 138A.

The young foliage is near Green, 137A, washed heavily with near Red, 53A, on its upper surface. The under surface is near Red, 53A.

The rachis is average in size, grooved on its upper side, with some stipitate glands on the edges. The under side is moderately smooth, with stipitate glands.

The stipules are medium-length to long, medium-width, with medium-length to long points turning out at an angle of more than 45°.

The plant displays a more than average resistance to mildew when compared to other commercialized varieties grown under comparable conditions in Ontario, Calif.

GROWTH

The plant is a dwarf variety, bushy and much branched. Its growth is vigorous, with canes which are medium to heavy caliper for miniature roses.

The main stems are near Yellow Green, 146A, in color. They bear few large prickles which are medium-length, almost straight to hooked slightly downward, with a moderately short broad base. The large prickles are near Greyed-Orange, 175C, in color. There are no small prickles and no hairs.

The branches are between Green, 143A, and Green, 139A, in color. They bear from few to several large prickles which are medium-length, almost straight to hooked slightly downward, with a moderately short broad base. These large prickles are near Greyed Orange, 164A, in color. There are no small prickles and no hairs.

New shoots are near Greyed Purple, 183C, in color. They bear several large prickles which are medium-length, almost straight to hooked slightly downward, with a moderately short broad base. The color of these large prickles is near Greyed Red, 182A. There are no small prickles and no hairs.

I claim:

1. A new and distinct variety of rose plant of the hybrid miniature class, substantially as herein shown and described, and being especially characterized in the profusion of its blooms throughout the growing season, and the uniformity of the coral and pink coloration of the same, said plant being vigorous and hardy and of somewhat higher than average resistance to mildew, under comparable growing conditions.

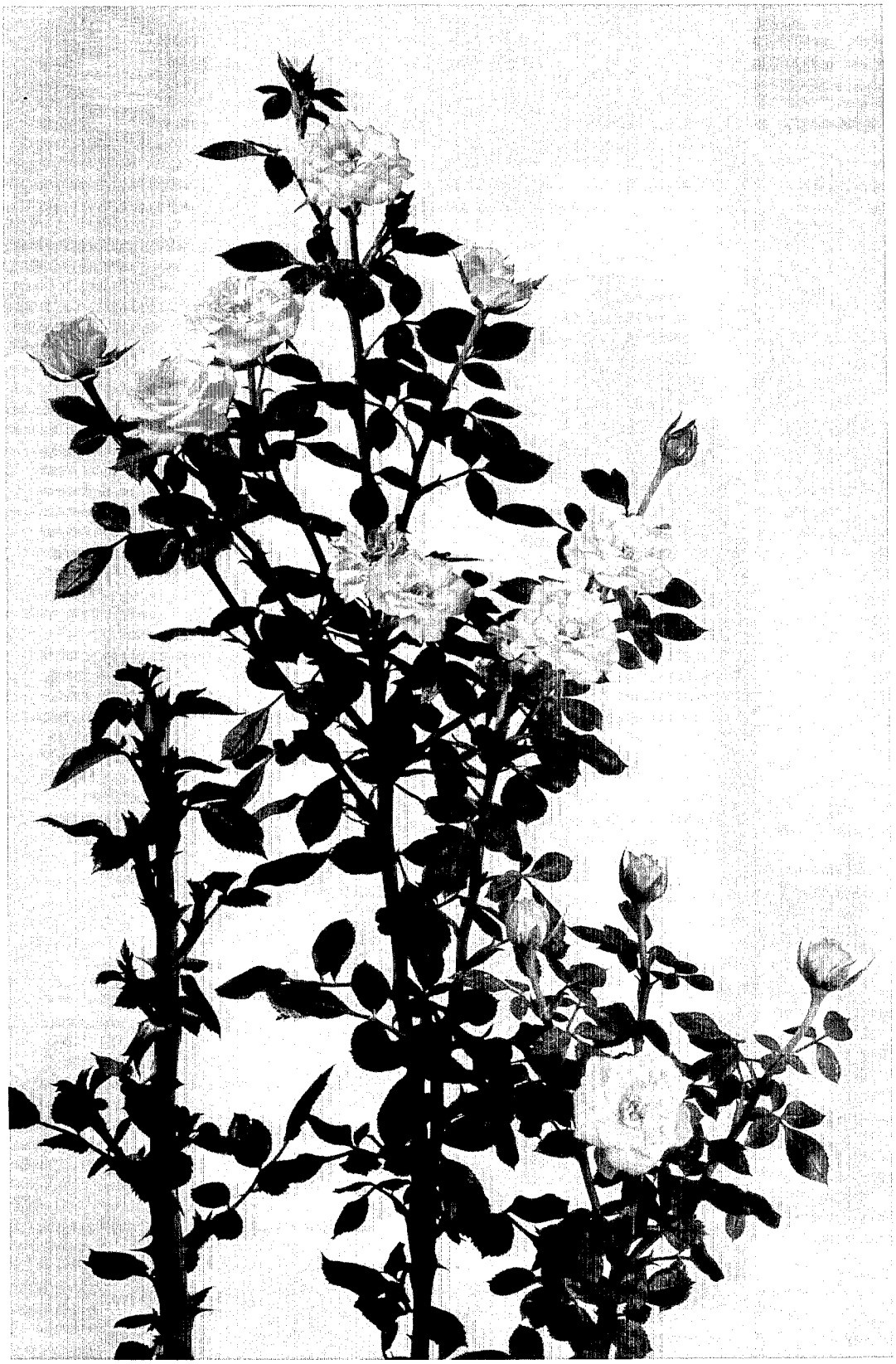

* * * * *